United States Patent
Vähäsalo et al.

(10) Patent No.: US 10,139,330 B2
(45) Date of Patent: *Nov. 27, 2018

(54) METHOD AND SYSTEM FOR ANALYZING SOLID MATTER CONTAINING LIQUIDS AND MONITORING OR CONTROLLING PROCESSES CONTAINING SUCH LIQUIDS

(71) Applicant: Kemira Oyj, Helsinki (FI)

(72) Inventors: Lari Vähäsalo, Littoinen (FI); Eija Saari, Espoo (FI); Iiris Joensuu, Espoo (FI); Marjatta Piironen, Espoo (FI)

(73) Assignee: KEMIRA OYJ, Helsinki (FI)

(*) Notice: Subject to any disclaimer, the term of this patent is extended or adjusted under 35 U.S.C. 154(b) by 0 days.

This patent is subject to a terminal disclaimer.

(21) Appl. No.: 14/403,579

(22) PCT Filed: May 24, 2013

(86) PCT No.: PCT/FI2013/050572
§ 371 (c)(1),
(2) Date: Nov. 25, 2014

(87) PCT Pub. No.: WO2013/175077
PCT Pub. Date: Nov. 28, 2013

(65) Prior Publication Data
US 2015/0114094 A1      Apr. 30, 2015

(30) Foreign Application Priority Data

May 25, 2012   (FI) .......................... 20125560

(51) Int. Cl.
*G01N 15/06*    (2006.01)
*G01N 30/00*    (2006.01)
(Continued)

(52) U.S. Cl.
CPC ......... *G01N 15/06* (2013.01); *G01N 15/0272* (2013.01); *G01N 30/0005* (2013.01);
(Continued)

(58) Field of Classification Search
CPC .. G01N 33/15; G01N 13/00; G01N 2013/006; G01N 21/9508; G01N 30/0005;
(Continued)

(56) References Cited

U.S. PATENT DOCUMENTS 3,449,938 A    6/1969  Giddings
5,087,823 A    2/1992  Silvy et al.
(Continued)

FOREIGN PATENT DOCUMENTS

CN    1212635 A    3/1999
CN    1271381 A    10/2000
(Continued)

OTHER PUBLICATIONS

Laitinen, O., "Utilisation of Tube Flow Fractionation in Fibre and Particle Analysis", University of Oulu, Jun. 11, 2011.
(Continued)

*Primary Examiner* — Hezron E Williams
*Assistant Examiner* — Marrit Eyassu
(74) *Attorney, Agent, or Firm* — Birch, Stewart, Kolasch & Birch, LLP

(57) ABSTRACT

The invention concerns a method and system for analyzing a liquid sample containing solid matter. The method comprises fractionating the sample according to particle sizes and/or masses of the solid matter so as to produce sample fractions, and measuring at least one physical or chemical property of at least one of said sample fractions. According to the invention the sample is conducted to a disintegration channel having one or more depressions, and a liquid flow having a non-constant temporal velocity profile is applied (Continued)

through the disintegration channel, in order to gradually take solid matter of the sample with the liquid flow from said one or more depressions for providing said sample fractions. The invention allows for efficient fractionation of samples, which cannot be fractionated using conventional field flow fractionation, for example.

21 Claims, 10 Drawing Sheets

(51) Int. Cl.
 G01N 15/02 (2006.01)
 G01N 15/00 (2006.01)
(52) U.S. Cl.
 CPC ......... G01N 2015/0053 (2013.01); G01N 2015/0288 (2013.01)
(58) Field of Classification Search
 CPC ........... G01N 15/06; G01N 15/0272; G01N 2015/0053; G01N 2015/0288
 USPC .............. 73/866, 865, 61.71; 435/288.7
 See application file for complete search history.

(56) References Cited

U.S. PATENT DOCUMENTS

| | | | | |
|---|---|---|---|---|
| 5,156,039 A * | 10/1992 | Giddings | ........... | G01N 30/0005 73/865.5 |
| 5,240,618 A * | 8/1993 | Caldwell | ........... | B01D 17/06 204/549 |
| 5,715,946 A | 2/1998 | Reichenbach | | |
| 5,900,159 A | 5/1999 | Engel et al. | | |
| 5,971,158 A * | 10/1999 | Yager | ........... | B01J 19/0093 209/155 |
| 5,972,190 A * | 10/1999 | Richman | ........... | G01N 27/44769 204/600 |
| 6,180,906 B1 * | 1/2001 | Trainoff | ........... | G01N 30/0005 209/127.1 |
| 6,423,237 B1 | 7/2002 | Guirguis | | |
| 6,562,307 B1 * | 5/2003 | Schuch | ........... | G01N 30/0005 422/255 |
| 6,641,708 B1 * | 11/2003 | Becker | ........... | B03C 5/026 204/547 |
| 2002/0036141 A1 * | 3/2002 | Gascoyne | ........... | B03C 1/00 204/547 |
| 2003/0049563 A1 * | 3/2003 | Iida | ........... | B01L 3/502761 430/296 |
| 2004/0000519 A1 | 1/2004 | Jiang et al. | | |
| 2004/0232074 A1 | 11/2004 | Peters et al. | | |
| 2008/0000833 A1 | 1/2008 | Peters et al. | | |
| 2008/0003689 A1 * | 1/2008 | Lee | ........... | G01N 30/0005 436/174 |
| 2008/0283402 A1 | 11/2008 | Peach | | |
| 2009/0301674 A1 * | 12/2009 | Niinimaki | ........... | D21B 1/32 162/49 |

FOREIGN PATENT DOCUMENTS

| | | | | |
|---|---|---|---|---|
| CN | 1345624 A | 4/2002 | | |
| CN | 1410155 A | 4/2003 | | |
| CN | 1613542 A | 5/2005 | | |
| EP | 1673975 A1 * | 6/2006 | ........... | A23C 9/1422 |
| EP | 1673975 A1 | 6/2006 | | |
| WO | WO 2007122289 A1 | 11/2007 | | |
| WO | WO 2010116030 A1 | 10/2010 | | |
| WO | WO 2011072396 A1 | 6/2011 | | |
| WO | WO 2012010744 A1 | 1/2012 | | |
| WO | WO 2012010745 A1 | 1/2012 | | |

OTHER PUBLICATIONS

Chinese Office Action issued in Chinese Patent Application No. 201380027299.3 dated Feb. 4, 2017, with English translation.

* cited by examiner

METHOD AND SYSTEM FOR ANALYZING SOLID MATTER CONTAINING LIQUIDS AND MONITORING OR CONTROLLING PROCESSES CONTAINING SUCH LIQUIDS

FIELD OF THE INVENTION

The invention comprises measurement and/or monitoring technology of industrial liquids containing solid matter. In particular, the invention concerns sampling of solid matter containing liquid, like aqueous suspensions or filtrates of forest industry, oil and mining industry and water treatment processes, and subsequent measurement of the samples. In more detail, the invention relates to an on-line analysis method and system utilizing fractionation technology of a sample flow.

BACKGROUND OF THE INVENTION

Monitoring of solid matter containing liquids in industrial processes can be carried out off-line or on-line. Off-line methods often involve batch sampling and laboratory analyses. They have the benefit of providing accurate and versatile information on the suspension but suffer from considerable time delays.

On-line methods, on the other hand, provide instant or almost instant information on the suspension, but the data that can be obtained is not as accurate as can be achieved in the laboratory. Some suspension properties cannot be measured using present on-line techniques.

An example of a remarkable area where measurements of solid matter containing liquids is needed is forest industry, in which wood pulp samples or filtrates, such as e.g. wire water or thickener filtrates, need to be monitored in order to be able to control the overall process. Further, e.g. solid matter containing liquids of oil and mining industry and water treatment industry, especially water reuse, desalination process, especially membrane processes, and cooling water treatment are of interest to be measured. Many such suspensions include particles, whose amount and size distribution have a considerable effect on upcoming process stages. E.g. agglomeration has, in fact, been shown to be the main threat for deposition and related runnability problems on paper machines. However, wood pulp and pulp industry originating liquids and filtrates have a strong tendency to flocculate, which makes the analysis of the solid matter therein challenging.

Some prior art pulp sample or filtrate monitoring techniques have utilized sample fractionation e.g. by filtration, centrifugation, sedimentation or column flow. The only known continuous fractionator is a column flow fractionator, also called a "tube fractionator". Tube fractionators are discussed e.g. in WO 2007/22289 and WO 2010/16030.

To date only the so-called flow cytometry technique has shown to be successful in detecting and assessing e.g. particle counts, size and/or type in pulp samples or filtrates originating from pulp and paper making industry. However, that technique is quite sophisticated and requires manual sample pretreatment in the laboratory before measurement. In addition, it cannot be used for online measurements. The advantage of flow cytometry measurements is that the particles in the solid matter containing liquid samples are very comprehensively characterized whereby also disturbing substances can be detected.

On the other hand, there are some lightweight techniques which provide on-line information on the level of amount of small particles in e.g. overall turbidity of samples. However, such information is not sufficient for all process control needs as the methods cannot differentiate different types of particles based, e.g. on hydrophobicity, particle size, and/or nature of the particles, whereby no detailed information is provided on disturbing substances. Such methods are discussed e.g. in WO 2012010744 and WO 2012010745.

Field flow fractionation (FFF) represents an approach in measurement of particles in non-industrial process samples. FFF was first described by J. C. Giddings in 1966 allows for physically separating particles having different physical properties from each other in a suspension. In FFF, a sample is injected to the FFF cell where the particles are subjected to a field e.g. temperature, electricity, gravitation, hence the particles in the sample sediment. A flow of liquid is passed through the cell perpendicular to the sedimentation field and as a result smaller (lighter) particles move faster in the flow direction compared to larger (heavier) particles. In a flow cell, particles travel in a laminar flow and heavy particles sediment faster than light particles and therefore heavy particles experience extra friction upon touching the flow cell walls compared to light particles. There are many different FFF systems available depending on the application and most notably on the particle size range one wants to fractionate. For example, there are sedimentation FFF (SdFFF) systems available where the gravitational field is induced through centrifugal force.

In normal FFF the Z-dimension of the cell is in the range of 100-500 µm. For paper pulp samples or filtrates thereof, these dimensions are way too small to achieve any notable separation. It is also typical that an SdFFF system is only capable of handling very small quantities of sample, which is below of what is needed for a paper mill sample as long as turbidity is used as the primary detector. The main problem with samples originating from industrial processes, e.g. with paper mill samples is the presence of fibers and especially fiber fines that have a strong tendency to flocculate in the FFF cell and thus block the cell. This makes the fractionation challenging as the flocks entrap also light particles.

Thus, prior art methods are unsuitable for separating light particles from heavier ones in many industrially important samples.

In addition to flocculation, another problem is the mechanical or chemical sticking of substances to each other and attaching of stickies and hydrophobic substances to surfaces of known fractionation systems, in particular those based on cross-flow filters or known FFF techniques. Hence, there exists a need for improved fractionation and analysis techniques for example for filtrates or pulp samples. A particular need exists for techniques which would additionally allow continuous on-line monitoring of water-intensive processes.

SUMMARY OF THE INVENTION

It is an aim of the invention to provide a new method and system for measuring/monitoring liquids containing solid particles, which overcomes at least some of the abovementioned problems. A specific aim is to provide a solution which allows for measuring samples which have a tendency to flocculate, i.e, they usually contain mechanically and/or chemically flocculating particles or substances causing flocculation of solid matter in the sample. For example, pulp and papermaking flocculating filtrates often contain fines. A further aim is to provide a method which suits for broad particle size and relatively large sample quantities and a broad particle size range to allow sufficient detector response.

A particular aim is to provide a new solution which allows for measuring the particle size and/or mass distribution of a filtrate or a pulp sample. A particular aim is to provide a new solution which allows for measuring the particle size distribution of an industrial liquid sample containing solid matter, e.g. filtrate sample, wood pulp sample or a filtrate of a wood fiber-containing liquid.

The aims are achieved by the method and system as defined in the independent claims.

According to one aspect, the present method of analyzing samples containing solid particles of different sizes or masses comprises fractionating the sample suspension according to particle size and/or mass so as to produce continuous sample fractions, and measuring at least one physical or chemical property of the sample fractions. The invention is based on the idea that the fractionating step comprises conducting the sample to a first channel, called herein also a disintegration channel, having one or more depressions. The disintegration channel, in particular the depressions therein, are designed so that when a liquid flow having a non-constant flow velocity profile is applied through the disintegration channel, the liquid flow disintegrates potential flocks in the sample and gradually takes particles of the sample with the liquid flow from said one or more depressions. The flow is conducted to a second channel, such as a field flow fractionation (FFF) channel or a channel operating according to the same principle as FFF channel, in which the separation continues and fractions for the measurement are finally produced.

The measurement may comprise one or more of the following: scattering measurement, turbidity measurement, fluorescence measurement, particle counting, imaging, or other preferably optical or acoustic measurement The sample or its fractions may also be stained in any stage of the process, i.e. before, during or after the fractionation, in order to aid optical measurement.

The system according to the invention for measuring sample suspensions containing solid particles of different sizes and/or masses comprising means for providing a batch sample from a process stream or container, means for fractionating the sample suspension according to particle sizes and/or masses so as to produce sample fractions, and means for measuring at least one physical or chemical property of at least some of the sample fractions. According to the invention the means for fractionating comprise a disintegration channel having one or more depressions and means for applying a liquid flow through the disintegration channel at a velocity producing hydrodynamic shear on the sample when interacting with said one or more depressions.

In one embodiment, the depressions are formed in a channel by consecutive widenings and one or more narrowings of cross sectional area in a channel so that depressions are formed between the narrowings at the region of the widenings. In one embodiment, the depressions are formed by protruding depression-defining walls inside a channel.

In a preferred embodiment, the sample to be analyzed comprises settleable matter. In a further embodiment, the sample comprises settleable matter having a tendency to flocculate.

In one embodiment, the first channel is placed in front of the second channel which further fractionates the sample, which is disintegrated and typically also pre-fractionated, in the first channel during the analysis.

In one embodiment, the depressions and liquid flow velocity profile are adapted to cause local changes in the flow field(s) of liquid in the first channel, but such changes do not take place in the second channel, at least at some flow velocities.

The depressions and liquid flow velocity profile may cause changes in the local direction of the flow or local velocity of the flow, or both. The flow may be temporally steady or unsteady by nature. In a preferred embodiment, the flow is, however, not turbulent, but generally speaking the existence of turbulent motion at some flow velocities is also not excluded.

In one embodiment, the flow is steady at some flow velocities of the fractionation process but becomes unsteady at higher flow velocities during the fractionation process.

As mentioned above, the depressions, in the disintegration channel are designed to provide local change(s) in the direction and/or velocity of the flow, and therefore make the flocks experience shear forces. The shear forces cause a disintegrating effect in the disintegration channel. The magnitude of the flow changes and shear forces generally increase when the average flow velocity in the channel is increased. The flow may also be unsteady at some or all points of the channel at least at some flow velocities.

According to one embodiment, the fractionation is a continuous process and said measuring is carried out on-line while the fractionation proceeds.

These and further advantageous embodiments are the subject of the dependent claims.

The invention provides significant advantages. First of all, by means of the invention, it is possible to separate smaller particles from agglomerates in flocculating samples in such a way that they can be easily detected. The invention does not require expensive instrumentation, since a simple piping with a suitable cross-sectional profile along its length is the key to efficient fractionation. Suitable designs are described later in this document.

The invention is based on the finding that due to the flocculation problem, a hydrodynamic shear has to be applied on the sample, in order to disintegrate the flocks. The shear is conveniently achieved with various embodiments of the invention using a local flow field change-causing disintegration channel. Due to local changes in the flow field (i.e. changes in flow velocity and or direction), shear forces take place which disintegrate the flocks and separate particles. Most conveniently this is achieved by the provision of abovementioned depressions which in the beginning restrain particles but allow them to be gradually taken with the liquid flow as the shear increases and more and more flocks disintegrate.

A particularly efficient fractionation is achieved by shaping and dimensioning the disintegration channel and selecting the temporal velocity profile such that essentially at all times, a portion of the particles sediment to the bottom of the depressions and a portion is continuously raised by the liquid flow from the depressions to a through-flow zone in the disintegration channel.

Air bubbles are very problematic since they may give response in the sensor, e.g. turbidity sensor, but they also interfere with the fractionation. Especially for on-line applications such a pressure producing pump might breakdown and be a threat to system reliability. Air bubbles may arise if the liquid flow is repeatedly accelerated and decelerated in short cycles using a pump. Since in the present invention the shape of the disintegration channel is the main cause for disintegration, the present method can be implemented using relatively slow and/or few flow velocity changes, whereby no air bubbles are formed.

Experimental results of the present method show very good correlation between the existing flow cytometry technique and the system according to the invention, with regard to particle size distribution of a sample or selected part of the sample. In these experiments, a turbidity sensor, fluorometer and image analyser were used as particle detectors.

However, the invention can generally be applied for any sample sizes. The sample size may vary for example between 5 ml and 100 ml. The particle size is also not limited to particles below ca. 100 µm, such as some prior art methods.

The invention allows for building on-line monitoring and/or control systems in which batch samples are taken from a process stream or process container and measured in repeated manner, for example at a frequency of 0.5 times/hour or more, in particular 1 time/hour or more. Following the measurements, there may be a step of determining the need for changing one or more process parameters, such as the rate of addition of one or more chemical agent, and corresponding step of changing such parameter should such need emerge.

The term "depression" means a structure having a zone with a wall surface level lower than the wall surface level of its surroundings and placed in such a way in the disintegration channel that the sample liquid (and particles therein) can enter there under gravitational force.

The term "field flow fractionation" (FFF) herein means a separation technique where a field is applied to a fluid suspension or solution pumped through a separation channel, perpendicular to the direction of flow, in order to cause separation of the particles present in the fluid, dependent on their differing mobilities under the force exerted by the field. Herein, the field is typically a gravitational field.

The term "temporal velocity profile" herein means a sequence of at least two differing flow velocities which are applied one after another during the separation process.

Next, embodiments and advantages of the invention are described in more detail with reference to the attached drawings.

DETAILED DESCRIPTION OF EMBODIMENTS

Overall Process

Figure 1:
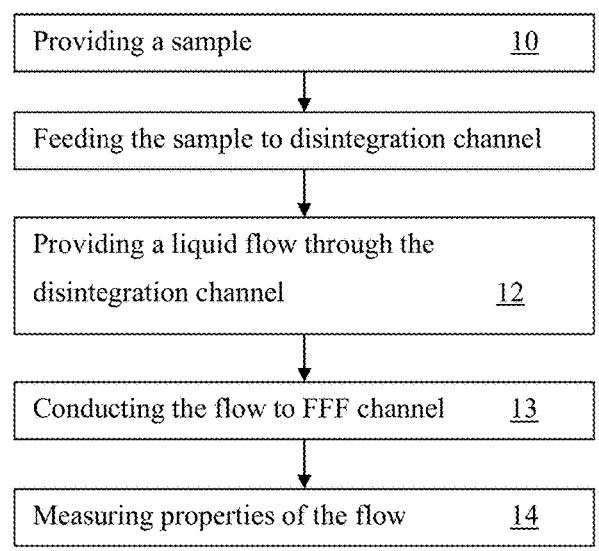
FIG. 1 shows a flow chart of the method according to one embodiment of the present invention.

With reference to FIG. 1, according to one embodiment, the present method comprises a sequence of several phases. In phase 10, a sample is provided from a process to be monitored or controlled. Typically, the sample is a batch sample which is taken using automated sampling means. Next, in phase 11, the sample is fed to a disintegration channel according to the invention. As will be explained later in more detail, it is preferred to drive the sample relatively fast to the channel so that it experiences rapid local accelerations which break potential flocks in the sample. It should be noted that the sample should preferably not be fed such that part of the sample passes the disintegration channel, since the idea is to retain the sample in its entirety in the channel and in particular its depressions until the start of the next phase.

In phase 12, a liquid flow, typically water flow, is conducted through the first channel from where it proceeds to a further fractionation channel, which is preferably an FFF channel with essentially or entirely laminar flow properties. This phase is denoted with the reference numeral 13. First, only the lightest particles (such as colloid sand dispersed pigments of pulp filtrate) are first taken by the flow to the FFF channel, but as time passes and the velocity of the liquid flow is increased, also heavier particles (such as aggregates) are taken. The velocity is increased to a level which catches even the heaviest (or at least the weights of interest) particles. As a consequence, the sample is effectively fractionated.

The desired properties of the fractionated sample are measured in phase 14. Typically, the measurement involves an optical or acoustic measurement, but there may be also alternative or additional measurement stages.

There may also be one or more pre-treatments stages, where the fractions are prepared for the measurement. Such pretreatment may comprise e.g. staining of the sample or particles of the sample before first channel or during fractionation.

The disintegration and fractionation phases 12 and 13, and typically also the measurement phase 14, occur at least partly simultaneously in a continuous configuration. However, it is also possible to recover the fractions for subsequent separate measurements, if immediate on-line results are not needed.

The whole fractionation process may take, depending on the nature of the sample, for example, 2-120 minutes, typically 5-30 minutes.

Figure 2:
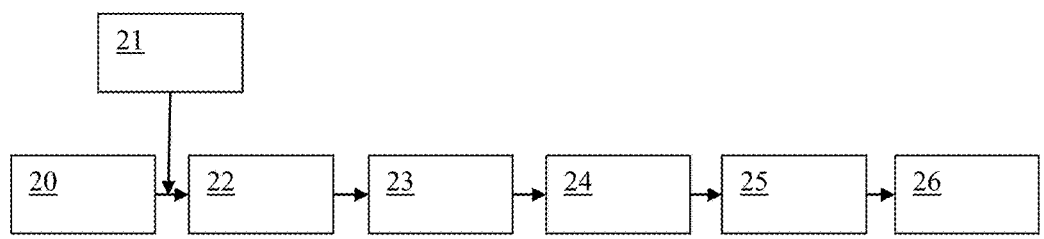
FIG. 2 shows a block diagram of various elements of the present measurement system according to one embodiment.

With reference to FIG. 2, according to one embodiment, the measurement system comprises a fractionator part 20, 21, 22, 23, 24, 25 and a measurement part 26. The fractionator part comprises a source of water 20 and a source of sample 21. A pump 22 is provided for driving the sample 21 or water 20 forward in the system using suitable ventilation (not shown). The pump is connected in forward direction to a disintegration channel 23 and further to an FFF channel 24. The main parts of the system, as described in FIG. 2 are 1) disintegration tube, 2) field flow fractionator cell and 3) homogenizer tube (25).

Figure 3:
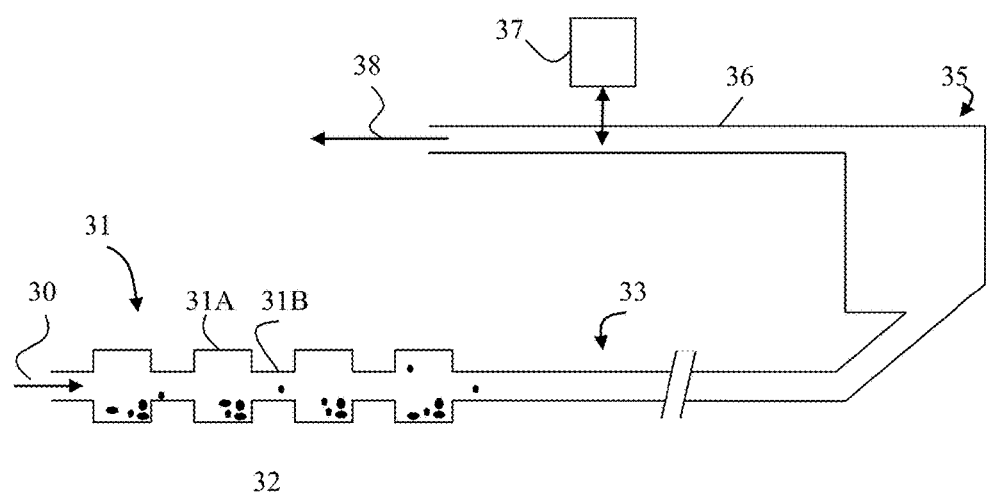
FIG. 3 shows a schematic illustration of a measurement system according to one embodiment of the invention.

In FIG. 3 there is shown in a more illustrative schematic view of the blocks 23-26 of FIG. 2. Sample and water input stream is denoted with the numeral 30 and output stream with numeral 38. The exemplary disintegration channel 31 is provided with widenings 31A and narrowings 31B such that depressions are formed to the region of the widenings 31A. The depressions serve as described above to disintegrate the flocs and to gradually release particles according to their size and/or mass to the FFF channel 33 following the disintegration channel 31. The fractionation proceeds in the FFF channel 33. The homogenizer tube 35, which is an optional part, comprises a vessel with a larger cross-sectional area than the FFF channel 33 and homogenizes the particle populations and flocs exiting the FFF channel into one population. From the homogenizer tube 35, the fractionated sample is conducted via a conduit 36 to a measurement device 37, which is arranged to measure the desired physical and/or chemical property of the sample.

Disintegration Channel

For example wood pulp and pulp filtrates such as wire water have a strong tendency to flocculate. This makes standard FFF techniques useless as the flocs entrap also light particles. Therefore, a hydrodynamic shear has to be applied on the sample in a disintegration tube, in order to disintegrate the flocs.

In the disintegration tube the sample goes through sections with high direction and/or velocity changes and consequently the sample is dispersed. Large or heavy particles exit the tube later compared to small or light particles, hence the disintegration tube also produces some pre-fractionation of the sample before the sample is fed to the field flow fractionator.

The necessary direction and/or velocity changes and "holding" of the non-disintegrated and large flocks and particles are achieved by means of depressions in the channel. The depressions can be formed in various ways, some of which are illustrated in FIGS. 7a-7f.

Figure 7A:
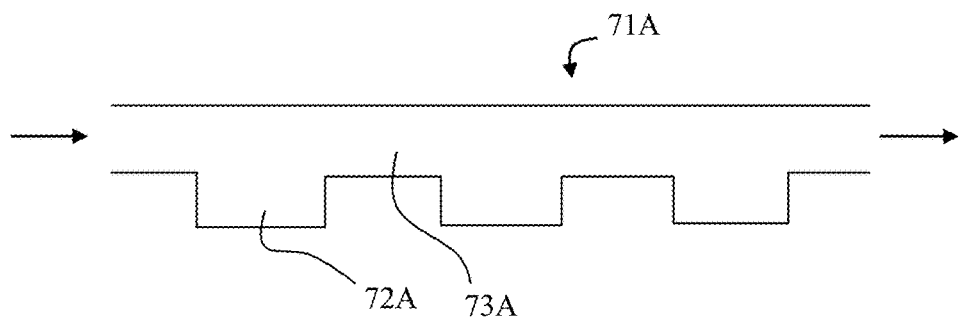
FIGS. 7a-7f show various embodiments of a dispersion channel provided with depressions.

FIG. 7a shows a disintegration channel 71A having consecutive depressions 72A formed by widenings and narrowings 73A, the bottom of the depressions 72A being at a lower level than the bottom of the narrowings 73A. The upper wall of the channel 71A is flat.

Figure 7B:
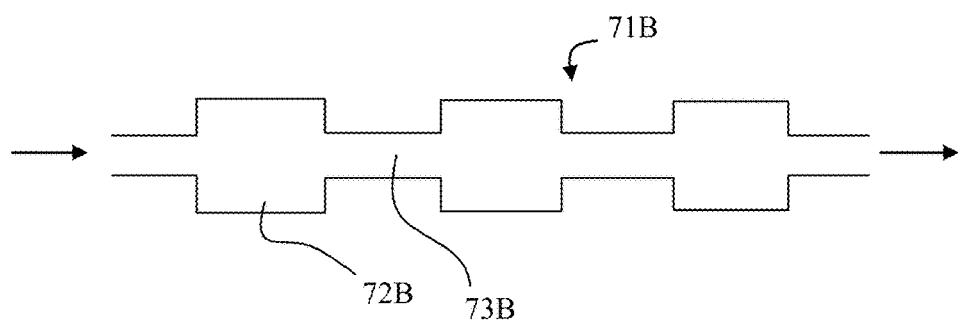

FIG. 7b shows a disintegration channel 71B having also consecutive depressions 72B and narrowings 73B. In this embodiment, the upper wall of the channel 71B in the region of the depressions 72B is also raised with respect to the region of the narrowings 73A. The depression-forming widenings may extend symmetrically to both vertical directions (as well as to horizontal directions, if desired). The upwardly extending widenings may serve to aid in disintegrating and/or retaining flocks in the disintegration tube 71B.

Figure 7C:
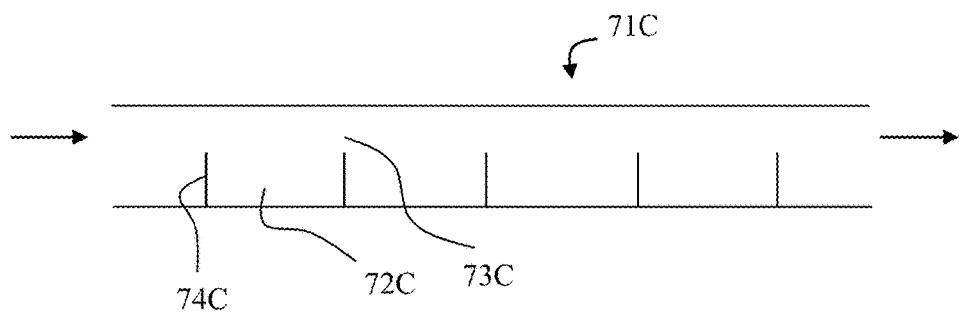

FIG. 7c shows a disintegration channel 71C wherein the depressions 72C have been formed by placing upwardly extending walls 74C to the bottom of an otherwise constant-diameter channel. Two adjacent walls 74C define a depression 72C between them and have the effect that local narrowings 73C are formed to the channel.

Figure 7D:
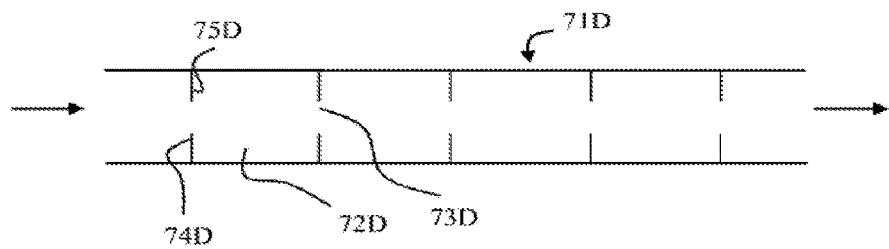

FIG. 7d shows a variant of the embodiment of FIG. 7c. In addition to first walls 74D in the bottom, there are also second walls 75D in the top wall of the channel. The depressions 72D are formed between the first walls 74D and narrowings 73D between aligned first and second walls 74D, 75D. The second walls 75D may serve to aid in disintegrating and/or retaining flocks in the disintegration tube 71D.

Figure 7E:
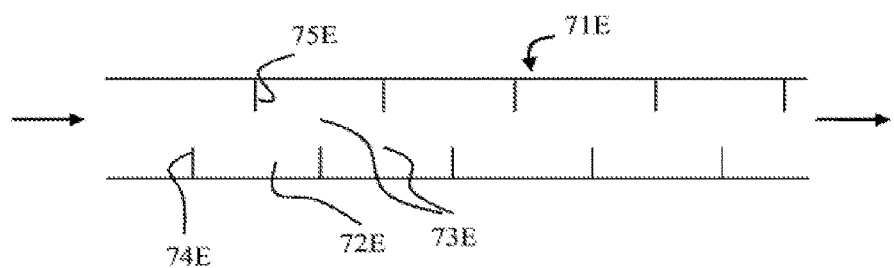

FIG. 7e shows a variant of the embodiment of FIG. 7e. The second walls 75E in the top wall of the channel are not adjacent to the first walls 74E but interleaved with them. The depressions 72E are formed between the first walls 74E and narrowings 73E between first and second walls 74D, 75D and the channel walls. The second walls 75D may serve to aid in disintegrating and/or retaining flocks in the disintegration tube 71D.

Figure 7F:
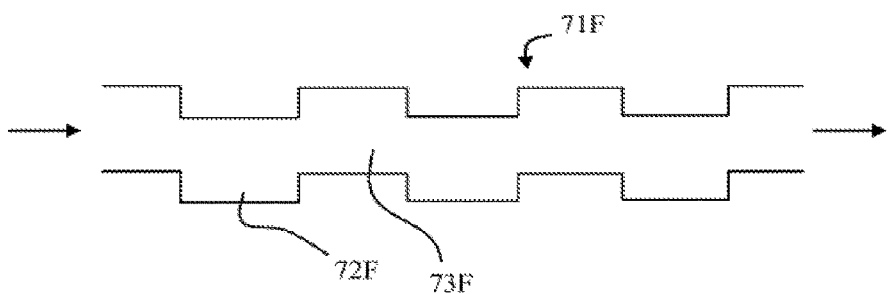

FIG. 7f shows a variant of FIGS. 7a and 7b. In this embodiment, the disintegration channel 71F is an upwardly and downwardly meandering channel, wherein the low regions of the meander form the depressions 72F. The oppositely extending regions 73F may aid in disintegrating the flocks, as compared with the flat top wall configuration of FIG. 7a.

To give some non-limiting examples, the inner cross-sectional area of the disintegration channel may vary from 1-500 mm$^2$ at the region of the narrowings to 3-1500 mm$^2$ at the region of the depressions. The number of depressions may on the other hand vary between 1-100, in particular 2-20. Usually, 2-10 depressions will provide sufficient disintegration.

The cross-sectional shape of the disintegration tube, may be almost any, including rectangular, circular and elliptical shapes, in all of the embodiments described above. The widenings and narrowings of the channel may also have different cross-sectional shapes with respect to each other. Also the transitions between the different regions of the channel and the wall shapes may be different than those schematically illustrated in the drawings. In particular, there may be non-vertical depression walls instead or in addition to vertical walls illustrated.

As briefly described above, the fractionation operation starts by feeding a plug of sample into the disintegration channel of the fractionator system. For this reason, the total volume of the disintegration channel preferably exceeds that of the sample. Thereafter a flow of water is fed behind the sample plug forcing the liquid of sample plug forward. The sample is in this way fed through the disintegration channel, where for example fibre flocks are disintegrated and proceed to further separation and detection.

According to one embodiment, in this part of the system disintegration effect is achieved by forcing the sample to flow through shape changes, like volume compressions of the pipe resulting in velocity and/or direction changes. In the disintegration channel, also some pre-fractionation occurs because particles of different mass will sediment at a rate according to their mass to the depressions. In addition, the particles with higher mass experience more friction as they bounce forward on the bottom of the channel. Dissolved and colloidal substances (DCS) will move forward in the cell essentially without sedimenting and thus experiencing friction.

FFF Channel and Homogenizer Tube

The purpose of the FFF channel is to arrange particles according to their sizes and/or masses. For example, fibers and colloids are separated from small particles. The separation is based on the fact that large and/or heavy particles experience larger flow resistance, i.e. friction, in the channel and are located in the bottom of the channel. However, the more the liquid flow velocity is increased, the heavier particles are taken by the stream. As a result, the particles are physically separated from each other. A prerequisite for efficient separation is that there are no large flocks in the FFF channel, which is ensured by the disintegration channel.

In a simplest form, the FFF channel in the present system may comprise a tube, for example a circular, elliptical or rectangular tube, which in long compared with its largest diameter and has a constant cross-sectional profile. The length-to-diameter ratio may be, for example, at least 20, preferably at least 50, typically at least 100. According to one embodiment, the cross-sectional area of the FFF channel is at least the same as the largest cross-sectional area of the disintegration channel. In practice, the cross-sectional area of the FFF channel may be, for example 1-2000 mm$^2$, typically 50-500 mm$^2$.

Some flocculation of fines and fibers may occur in the field flow fractionator cell. However, this flocculation does not entrap the smallest particles since sufficient pre-fractionation has already been achieved in the disintegration tube. The particle populations and flocks exiting the field flow fractionation cell are homogenized into one population in the homogenizer tube. Especially flocks of fines tend to exit the field flow fractionator cell tens of seconds apart from each other. The idea with the homogenizer tube is to mix these flocks or same type of particles into one homogeneous population. After the homogenizer tube the sample goes to a detector.

Flow Velocity Profile

In order to gain the best possible separation of the particles, the flow velocity of the sample has to be varied during the analysis. i.e. the temporal velocity profile of the flow is non-constant. Initial flow velocity often has to be very slow, in order to separate the light particles from the larger or heavy ones. In order for the larger or heavy particles to pass through the system the flow velocity has to be increased toward the end of the sample run.

It is preferred that the flow velocity is adjusted such that the depressions provide at least locally unsteady motion of the liquid flow at least at some stage of the process. According to one embodiment the velocity profile comprises at least one profile part with a gradually or stepwise increasing velocity as a function of time, the highest flow velocity in that profile part being at least 5 times, preferably at least 10 times, in particular at least 25 times higher than the lowest flow velocity in said profile part.

To give some examples, the sample may be driven into the disintegration tube at a first flow rate (e.g. 3 ml/s). Then, water is fed at a flow rate which is in the beginning considerably smaller than the first flow rate (e.g. 0.2 ml/s) and gradually raised to be considerably higher than the first flow rate (e.g. 10 ml/s). In the slow flow stage, only the finest particles proceed to the FFF channel and in the high flow rate, also the heaviest particles in the system proceed to the FFF channel and further to measurement.

The whole sequence may take, for example, 2-20 minutes. After the sequence, a new sample batch can be analyzed, optionally washing the measurement system in between the analyses.

It is also likely that different types of samples (e.g. pulp samples, wire water samples, fine paper samples, SC samples, LWC samples, and different types of samples in other fields of industry) have to be run with different operation parameters (flow velocities and duration).

Measurement

According to one embodiment, the measurement device 37 is an optical measurement device, including devices capable of imaging. According to an alternative embodiment, the measurement device 37 comprises an acoustic measurement device.

According to one embodiment the measurement device 37 comprises a turbidity sensor and/or a fluorometer.

The optical or acoustic measurement device may be arranged to measure any or more of the following: light scattering of particles, turbidity of the sample, fluorescence of particles, hydrophobicity of particles based on fluorescence, quenching, the number or density of particles, or an optical or acoustic two or three-dimensional image of the sample where at least some of the particles can be distinguished. If the sample is imaged, the system is preferably equipped with image analysis unit, configured to measuring at least one parameter describing particle mass, size and/or chemical nature from the image obtained. Imaging is a particularly preferred option if there is a need to determine the chemical nature of the particles in the sample, as for example the transparency, density, color and coarseness visible in the images are descriptive of chemical nature.

Application Areas

The invention can be used for fractionating and analyzing any samples containing free solid matter units or solid matter flocks that can be disintegrated. Important examples are pulp suspension or filtrate from a pulp or papermaking process. Additional examples are sample from oil, mining or water treatment process, in particular desalination processes, membrane processes, cooling water treatment, water reuse.

In industry, the two main application areas of the invention are monitoring of processes and control of processes, in particular control of addition rate of one or more process chemicals.

"Controlling" comprises the decision and action of changing one or more process parameters and the decision of not changing the process parameters (=keeping the parameters constant). Controlling can be carried out manually, semi-automatically or automatically based on the analysis according to the invention.

"Controlling the addition rate of a chemical agent" covers controlling of volume flow per time unit and/or controlling of concentration of a chemical agent added to the process flow. In particular, the chemical agent may be one that affects the physical or chemical property being measured according to the invention. This allows for efficient quality control of process streams.

EXAMPLES

A laboratory prototype according to the illustration of FIG. 3 has been successfully tested and found to be able to produce an acceptable disintegration and pre-fractionation of the sample before the sample is fed to a second cell for further fractionation. The laboratory prototype comprises a disintegration tube which is installed before the fractionator cell. The disintegration tube comprised 4-5 wider (inner diameter 9 mm) and 3-4 narrower (inner diameter 5 mm) tubes connected sequentially to each other. The length of each section was 3-8 centimeters.

The cross sectional area of the FFF channel, which herein was a circular hose, was 133 mm$^2$ and the length was 1.5 m.

The prototype was used to demonstrate the effect of the invention according to the Examples below.

Example 1

Figure 4:
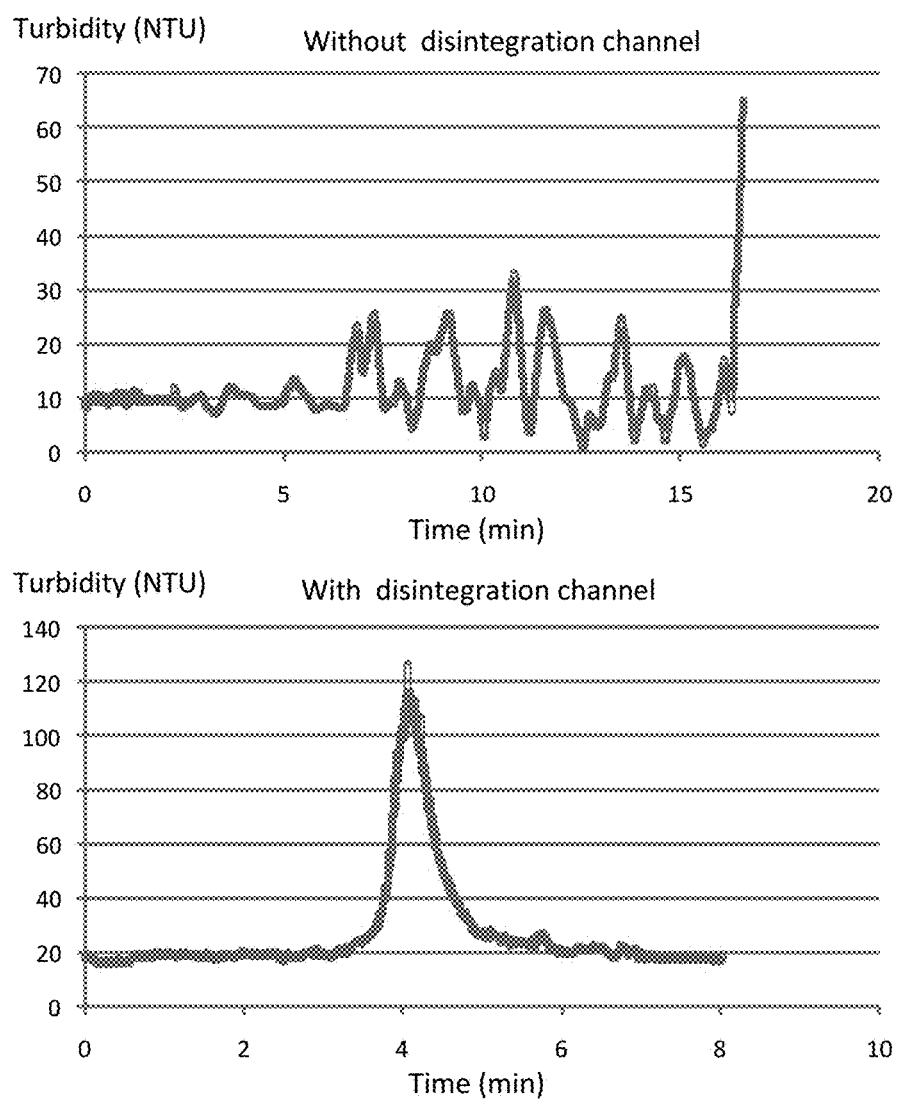
FIG. 4 shows an example of a TMP-pulp sample run through the same field flow fractionator cell without a disintegration channel (upper) and with a disintegration channel (lower).

The effect of the disintegration tube is essential for a successful separation. FIG. 4 shows two runs in the same field flow fractionator cell with (lower graph) and without (upper graph) a disintegration tube. The sample contained mainly TMP fines. Without the disintegration the fines flocculated in the cell and therefore, particles of same mass did not exit the cell at the same time (upper graph). However, when the disintegration was used, all the fines exited the cell as a uniform population (lower graph). It is clear that without disintegration the required level of separation is not achieved due to heavy flocculation.

The measurement device comprised an on-line turbidity sensor.

Example 2

Figure 5:
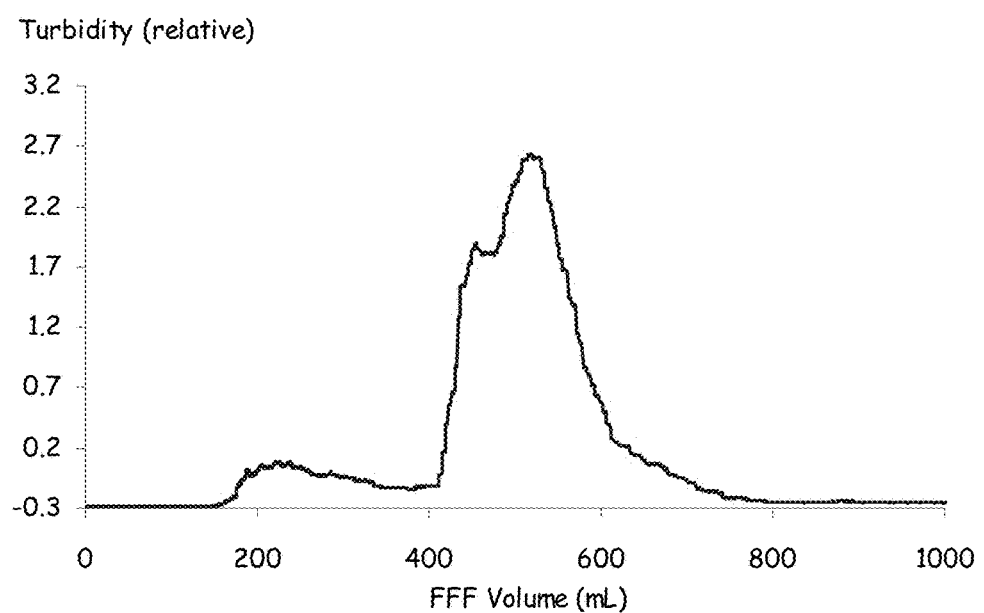
FIG. 5 shows a comparison chart of the results obtained with a fractionator according to the invention.

FIG. 5 illustrates analysis results of a wire water sample from a fine paper machine analyzed according to the invention. Such samples contain both small and large particles.

The large particles in this case are pigment aggregates and the small particles mainly dispersed pigment and wood fines. It can be seen that the respective peaks are clearly shown in a turbidity measurement following the present fractionation process. Large particles elute through the system much later than the small particles.

The results were compared to and the fractionation efficiency was evaluated by flow cytometry. Comparison indicated similar particle distributions and therefore proved that the present fractionator system is capable of separating the two main particle size populations very reliably and accurately.

Figure 6:
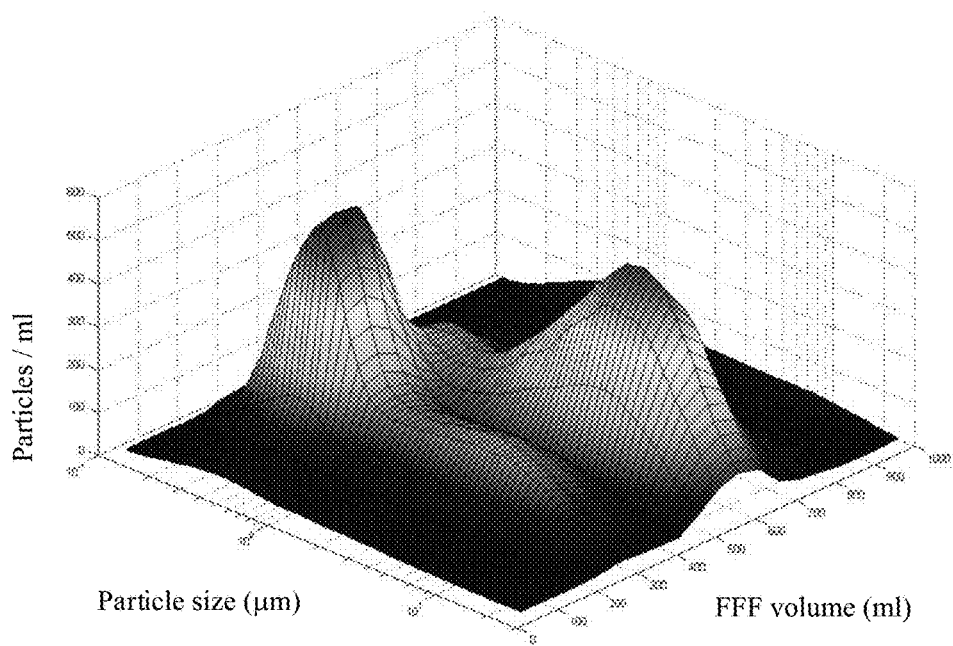
FIG. 6 shows a comparison of flow cytometry particle size and the disintegration channel assisted field flow fractionator.

In FIG. 6 the same sample as shown in FIG. 5 is presented as particle size distributions of the different 50 mL fractionator samples. During the fractionation run the sample passing the system was fed into 50 mL sample tubes which were then analyzed by flow cytometry for particle size. From the results it is clear that the fractionation can be seen, without overlapping of the small particles in the fractions with the large aggregates.

Example 3

Figures 8A, 8B:
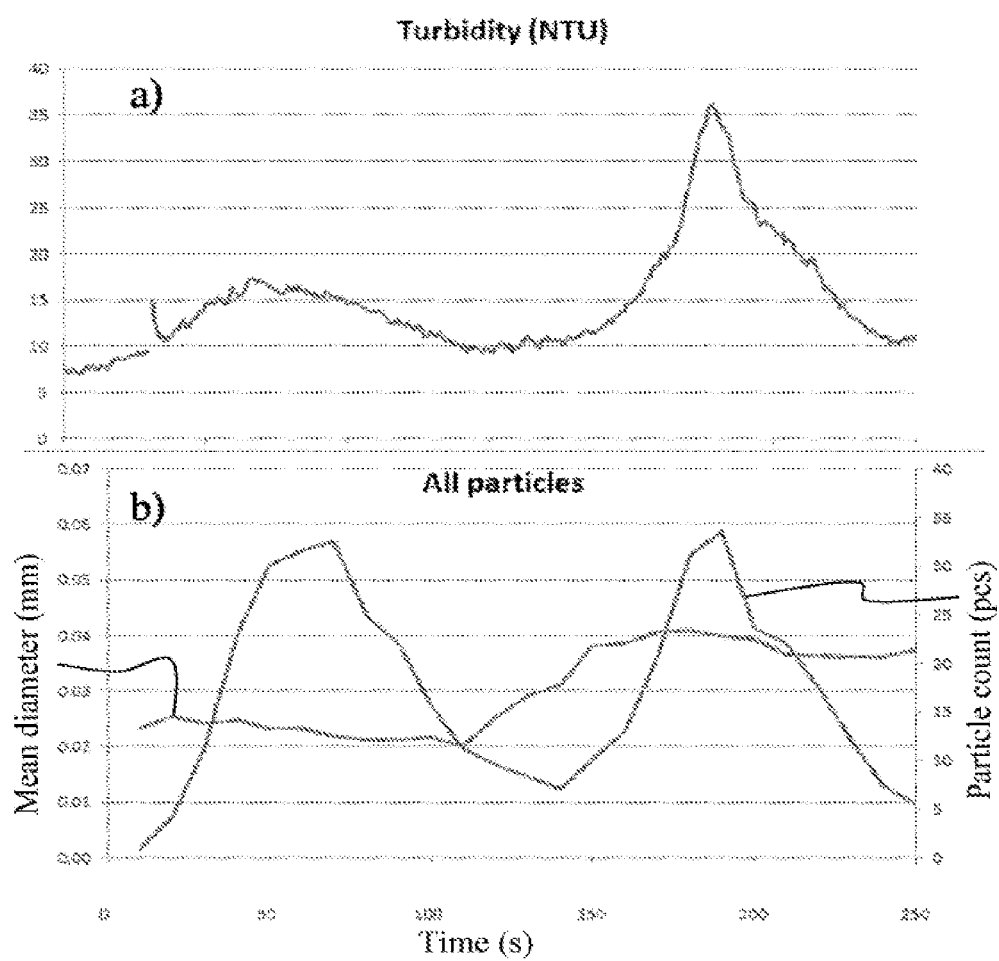
FIGS. 8a-d shows as graphs measurement examples obtained in a sample run using a) turbidity sensor and b-d) image analyzer.
Figures 8C, 8D:
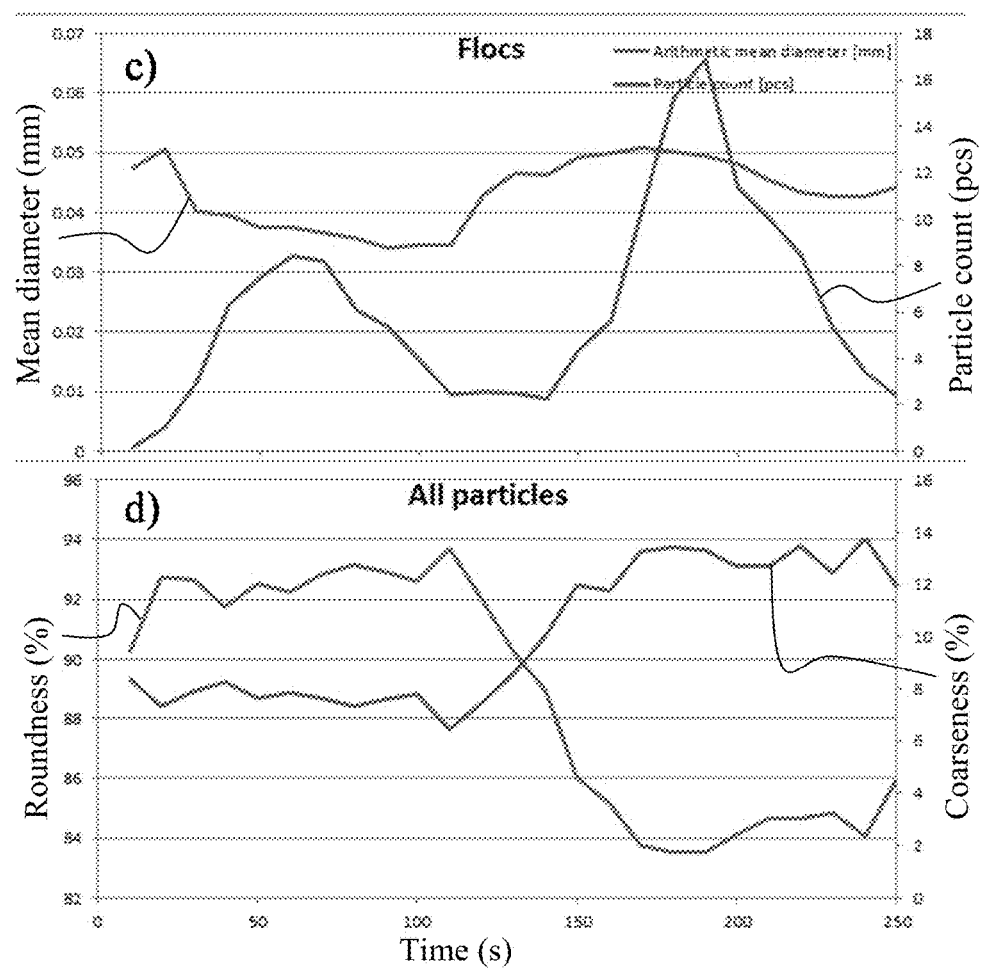

FIGS. 8a-8d shows an example of a sample run through the system including online turbidity sensor and image analyzer. The sample was a wire water sample. Turbidity trend shows that the system separates the particles of the sample into two populations (FIG. 8a). Image analysis results show (FIGS. 8b and 8c) that the lightest/smallest particles are coming first from the disintegration and FFF channels. The mean diameter of detected particles is ~25 µm in the first population. The mean diameter of particles in the second population is 50 µm. The shape factors (roundness and coarseness) of particles change as a function of time (see FIG. 8d) indicating that the type of the particles in these two populations is different. Mean roundness value of particles is higher in the first population meaning that they are more spherical Coarseness value of particles is higher for the second population.

This example shows using a plurality of different measurement techniques and parameters observed that the present fractionation method is capable of arranging the particles well according to their physical and chemical properties.

Example 4

Figure 9:
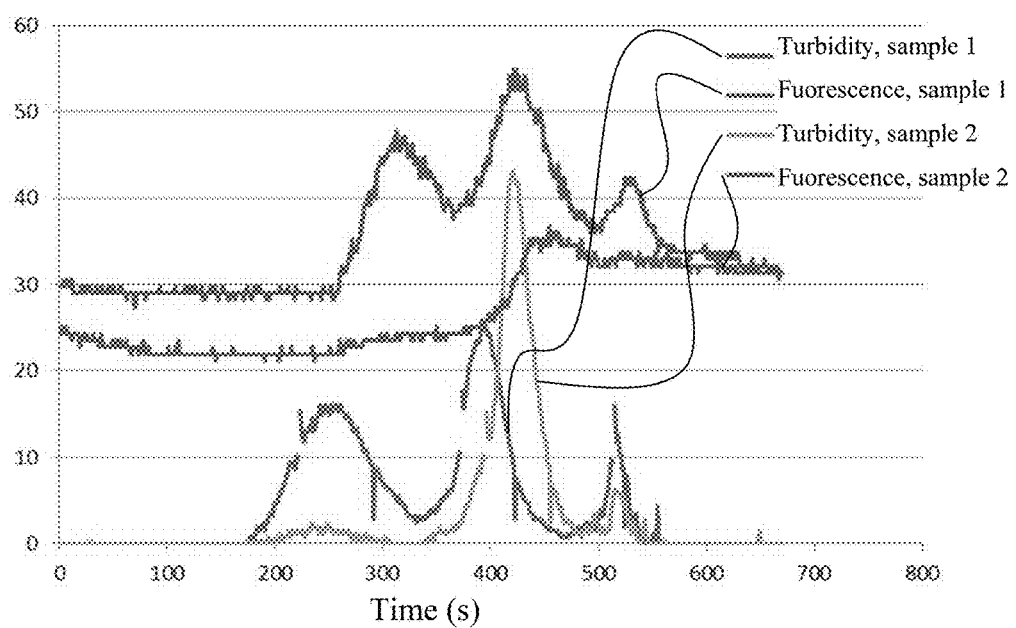
FIG. 9 shows as a graph measurement example of two other sample run using a turbidity sensor and a fluorescence sensor.

FIG. 9 shows an example of the results obtained for two different water samples (wire water). Samples were run through the measurement system equipped with an online turbidity sensor and with an online fluorescence sensor. The first turbidity peak (at 200-350 seconds) shows the presence of light/small particles and the second turbidity peak (at 350-500 seconds) shows the presence of heavier/larger particles. Fluorescence measurement shows the fluorescence level of the particles.

Also this example clearly evidences that the present method works well.

The invention claimed is:

1. A method of analyzing a liquid sample containing solid particles, the method comprising:

fractionating the sample according to particle sizes and/or masses of the solid particles, so as to produce sample fractions, by
conducting the sample to a disintegration channel having depressions to retain the sample in said depressions, and a through-flow zone,
applying a liquid flow having a non-constant temporal velocity profile through the disintegration channel, in order to gradually release solid particles of the sample with the liquid flow from said depressions to the through-flow zone in the disintegration channel, wherein the liquid flow is applied at a velocity producing hydrodynamic shear on the sample when interacting with said depressions, to disintegrate flocks in the sample retained in said depressions, and
measuring at least one physical or chemical property of at least one of said sample fractions.

2. The method according to claim 1, wherein the particles of the sample are gradually released with the liquid flow from said depressions as the flow velocity is varied.

3. The method according to claim 1, wherein the liquid flow and the depressions cause the hydrodynamic shear on the sample.

4. The method according to claim 1, wherein the number of depressions in said disintegration channel is at least 2.

5. The method according to claim 1, wherein said fractionation is a continuous process and said measuring is carried out on-line while the fractionation proceeds.

6. The method according to claim 1, wherein the solid particles in the sample have a tendency to flocculate mechanically or chemically.

7. The method according to claim 1, wherein the sample is conducted to the disintegration channel at a velocity which causes initial disintegration of sample due to shear forces.

8. The method according to claim 1, wherein after conducting the sample to the disintegration channel, sample flow is stopped before applying the liquid flow.

9. The method according to claim 1, wherein the velocity profile comprises at least one profile part with a gradually or stepwise increasing temporal velocity as a function of time, the highest flow velocity in said profile part being at least 5 times higher than the lowest flow velocity in said profile part.

10. The method according to claim 1, wherein the liquid flow, with particles taken from the disintegration channel, is conducted from the disintegration channel to a field flow fractionation (FFF) channel.

11. The method according to claim 1, wherein the liquid flow is conducted from the disintegration channel to a homogenizer channel having an average diameter larger than the average diameter of the disintegration channel.

12. The method according to claim 1, wherein said measuring of at least one physical or chemical property comprises measuring the turbidity, hydrophobicity of at least one of the sample fractions, particle size of the sample fractions and/or optical response of the solid particles in at least one of the sample fractions, or obtaining an image of at least one of the sample fractions.

13. The method according to claim 1, wherein the sample suspension is a raw or treated pulp sample or filtrate.

14. The method according to claim 1, wherein it is automatically carried out for on-line monitoring purposes for samples sequentially taken from a suspension of pulp-making process, paper or cardboard-making process, wastewater treatment process, desalination process, membrane process, or oil or mining process, or controlling of such processes.

15. A system for measuring sample suspensions containing solid particles of different sizes, the system comprising:
   means for providing a sample suspension,
   a disintegration channel, having
      a through-flow zone,
      depressions to retain the sample in said depressions, and
      a means for applying a liquid flow through the disintegration channel at a velocity producing hydrodynamic shear on the sample when interacting with said depressions, to disintegrate flocks in the sample retained in said depressions and to raise particles from the depressions to the through-flow zone in the disintegration channel, for fractionating the sample suspension according to particle sizes and/or masses so as to produce sample fractions, and
   means for measuring at least one physical or chemical property of at least some of the sample fractions.

16. The system according to claim 15, wherein the depressions are each formed by widenings and preceding and following narrowings in the cross-sectional area of the disintegration channel, along the flow direction.

17. The system according to claim 15, wherein the depressions are at least partly defined by walls in the disintegration channel.

18. The system according to claim 15, further comprising means for conducting the sample to the disintegration channel at a velocity which causes a temporally unsteady flow of sample.

19. The system according to claim 15, wherein the means for applying the liquid flow is to feed the liquid flow with a non-constant temporal velocity profile.

20. The system according to claim 15, further comprising a field flow fractionation (FFF) channel coupled in sequence with the disintegration channel for further fractionation of the sample.

21. The system according to claim 15, wherein the number of depressions in said disintegration channel is at least 2.

* * * * *